US00PP20463P2

(12) United States Plant Patent
Henny et al.

(10) Patent No.: US PP20,463 P2
(45) Date of Patent: Nov. 10, 2009

(54) ***AGLAONEMA* PLANT NAMED 'UF-742-3'**

(50) Latin Name: *Aglaonema commutatum*
Varietal Denomination: UF-742-3

(75) Inventors: Richard Henny, Tavares, FL (US); Jianjun Chen, Apopka, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/231,142

(22) Filed: Aug. 29, 2008

(51) Int. Cl.
*A01H 5/00* (2006.01)

(52) U.S. Cl. ..... Plt./376

(58) Field of Classification Search ..... Plt./376
See application file for complete search history.

*Primary Examiner*—Susan B McCormick Ewoldt

(57) ABSTRACT

A new and distinct variety of *Aglaonema*, denominated 'UF-742-3', has small to medium size and upright plant growth habit, vigorous and dense growth habit, very freely clumping habit, dark green-colored leaves with large grey green-colored venal areas covering over half the leaf surface, and white colored petioles.

2 Drawing Sheets

ACKNOWLEDGMENT OF FEDERAL RESEARCH SUPPORT

This invention was made with government support under FLA-APO-04158 awarded by the Cooperative State Research, Education, and Extension Service, USDA. The government has certain rights in the invention.

Botanical designation: *Aglaonema commutatum.*

Variety denomination: 'UF-742-3'.

BACKGROUND OF THE INVENTION

The present invention relates to anew and distinct cultivar of *Aglaonema* plant, botanically known as *Aglaonema commutatum,* and hereinafter referred to by the name 'UF-742-3'.

The objective of the Inventor's breeding program is to create new *Aglaonema* cultivars that have unique and attractive foliage coloration, uniform plant habit, and exceptional interior environment performance.

The new *Aglaonema* 'UF-72-3' originated from a cross-pollination made by the Inventors in Apopka, Fla. of *Aglaonema commutatum* cultivar Treubii (not patented), as the female, or seed, parent with *Aglaonema commutatum* cultivar Curtissi (not patented), as the male, or pollen parent. The new *Aglaonema* was discovered and selected by the Inventors as a single plant within the progeny of the stated cross-pollination in a controlled environment in Apopka, Fla.

Asexual reproduction of the new cultivar by tip cuttings in a controlled environment in Apopka, Fla. has shown that the unique features of this new *Aglaonema* are stable and reproduced true to type in successive generations of asexual reproduction.

SUMMARY OF THE INVENTION

The cultivar UF-742-3 has not been observed under all possible environmental conditions. The phenotype may vary somewhat with variations in environment such as temperature and light intensity, without, however, any variance in genotype.

The following traits have been repeatedly observed and are determined to be the unique characteristics of 'UF-742-3'.

These characteristics in combination distinguish UF-742-3 as a new and distinct cultivar of *Aglaonema:*

1. Small to medium size and upright plant growth habit.
2. Vigorous and dense growth habit.
3. Very freely clumping habit.
4. Dark green-colored leaves with large grey green-colored venal areas covering over half the leaf surface.
5. White colored petioles.

Plants of the new *Aglaonema* differ from plants of the female parent selection, the cultivar Treubii, in the following characteristics:

1. Plants of the new *Aglaonema* are smaller and more compact than the female parent selection.
2. Plants of the new *Aglaonema* produce leaves that are shorter and wider than the female parent selection.
3. Plants of the new *Aglaonema* differ in petiole color as plants of the female parent have green petioles and petioles of the new *Aglaonema* are white.

Plants of the new *Aglaonema* differ from plants of the male parent, the cultivar Curtissi, in the following characteristics:

1. Plants of the new *Aglaonema* have extensive grey green-colored venal areas and leaves of the cultivar Curtissi have very small areas of grey green-color associated with the venal areas.
2. Plants of the new *Aglaonema* and the cultivar Curtissi differ in leaf size as leaves of the new *Aglaonema* are less than half the size of leaves of the cultivar Curtissi.
3. Plants of the new *Aglaonema* and the cultivar Curtissi differ in petiole color as plants of the cultivar Curtissi have green-colored petioles.

Plants of the new *Aglaonema* can also be compared to plants of the cultivar Silver Ribbons, disclosed in U.S. Plant Pat. No. 12,985. In side-by-side comparisons conducted in Apopka, Fla., plants of the new *Aglaonema* differed from plants of the cultivar Silver Ribbons in the following characteristics:

1. Plants of the new *Aglaonema* were of an overall smaller size than plants of the cultivar Silver Ribbons.
2. Plants of the new *Aglaonema* had smaller individual leaf size than individual leaves of plants of the cultivar Silver Ribbons.

3. Plants of the new *Aglaonema* had leaves that are mostly smooth compared to twisting and undulating form of leaves of the cultivar Silver Ribbons.

BRIEF DESCRIPTION OF THE DRAWINGS

The accompanying photographs (FIG. 1 and FIG. 2) show the overall appearance of the new *Aglaonema*. These photographs show the colors as true as it is reasonably possible to obtain in colored reproductions of this type. Colors in the photographs may differ slightly from the color values cited in the detailed botanical description which accurately describe the colors of the new *Aglaonema*.

The left-most leaf in FIG. 1 shows a close-up view of the upper surface of a typical leaf of 'UF-742-3'.

Figure 1:
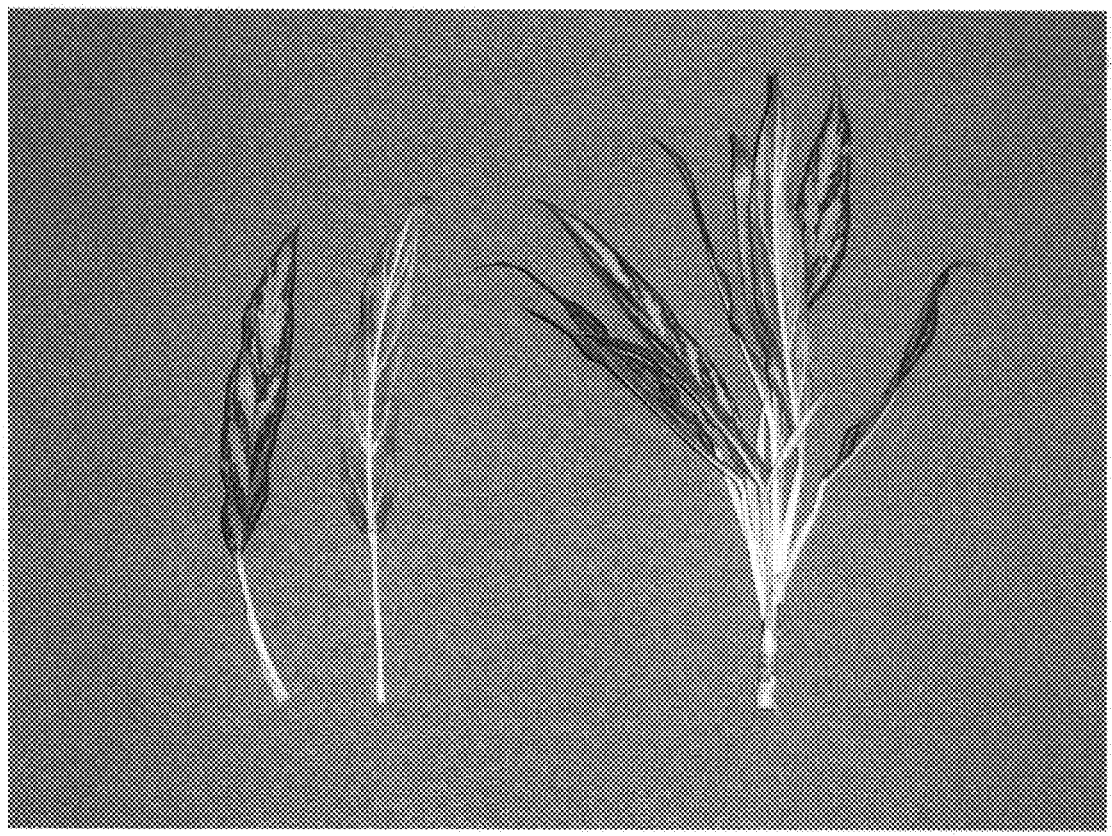

The second leaf from the left in FIG. 1 shows a close-up view of the lower surface of a typical leaf of 'UF-742-3'.

The stem and leaves on the right-most side of FIG. 1 shows at typical stem with 2 inflorescences present.

Figure 2:
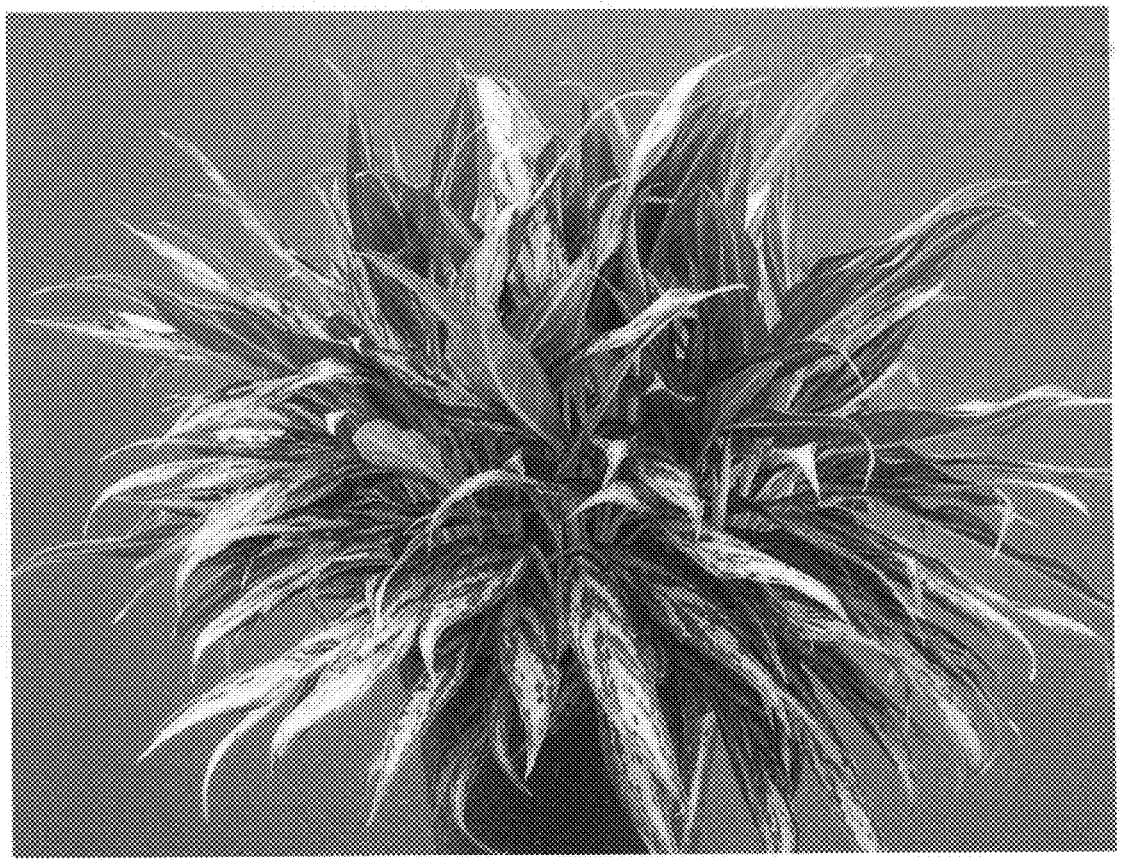

FIG. 2 is a side perspective view of a typical plant of 'UF-742-3' grown in a container.

DETAILED BOTANICAL DESCRIPTION

In the following description, color references are made to The Royal Horticultural Society Colour Chart, 2001 Edition, except where general terms of ordinary significance are used. The aforementioned photographs and following observations and measurements describe plants grown in containers in Apopka, Fla. during the spring and early summer in a glass-covered greenhouse. Plants were grown using practices and under conditions which approximate those generally used in commercial *Aglaonema* production. During the production of the plants, day temperature ranged from about 29° C. to 35° C., night temperature ranged from a bout 18° C. to 26° C. and light levels were about 2,500 foot-candles. Plants were grown from a single stem cutting and were about 12 months old when the photographs and the detailed description were taken.

Botanical classifiacation: *Aglaonema commnutatum* cultivar UF-742-3.

Parentage:

*Female, or seed, parent.*—*Aglaonema commutatum* cultivar Treubii, not patented.

*Male, or pollen, parent.*—*Aglaonema commutatum* cultivar Curtissi, not patented.

Propagation:

*Type.*—By tip cuttings.

*Time to initiate roots, summer.*—About 20–25 days at 25° C. to 35° C.

*Time to initiate roots, winter.*—About 28–35 days at 15° C. to 27° C.

*Time to produce a rooted young plant, summer.*—About 30–35 days at 25° C. to 35° C.

*Time to produce a rooted young plant, winter.*—About 40–45 days at 15° C. to 27° C.

*Root description.*—Abundant, fleshy whitish-colored roots with finer lateral roots.

Plant description:

*Plant/growth habit.*—Short compact plant habit; inverted triangle. Vigorous, dense growth habit; suitable for 15-cm to 20-cm containers. New leaves initially upright, then arching outwardly with development.

*Plant height, from soil level to top of leaf canopy plane.*—About 20 cm to 25 cm.

*Plant diameter or spread.*—About 40 cm to 48 cm.

*Stem description.*—Branching habit: Plants of the new *Aglaonema* are freely basal branching with about 8 to 10 basal branches developing per plant. Aspect: Mostly upright. Strength: Strong. Length, soil level to junction of two youngest leaves: 15 cm to 18 cm. Diameter: About 1.5 cm Internode length: About 7 mm to 9 mm. Color, immature: 137C mottled with 148C and 148D. Color, mature: 151C mottled with 148C and 148D; with further development, 153C to 153D mottled with 148C and 148D.

Foliage description:

*Arrangement.*—Alternate/whorled; simple.

*Length.*—About 17 to 22 cm.

*Width (flattened).*—About 3.3 cm to 3.9 cm.

*Shape.*—Lanceolate.

*Apex.*—Sharply acuminate.

*Base.*—Obtuse.

*Margin.*—Entire; mostly flat with some broad undulations.

*Texture, upper and lower surfaces.*—Smooth, glabrous.

*Venation pattern.*—Pinnate.

*Color.*—Developing leaves, upper surface: Background color, between 137B to 137C; venal areas 191B to 191C Venation: Midrib 137A to 137B; primary veins 137A. Developing leaves, lower surface: Ground color 138B uniform Venation: Midrib 138B; primary veins 138D. Fully expanded leaves, upper surface: Background color, 139A, venal areas, 191A to 191B. Venation: Midrib 191A in basal half, fading to 138B near the apex; primary veins 191C. Fully expanded leaves, lower surface: Background color, 137C; venal areas mottled with 155A to 155B. Venation: Midrib 155A to 155B, mottling associated with edges of midrib 155A to 155B; primary veins 155A to 155B.

Petiole:

*Aspect.*—Mostly erect, arching outwardly to about 30° from vertical with development.

*Length.*—8.5 to 9.5 cm.

*Diameter, distal.*—About 3 mm.

*Diameter, proximal, flattened.*—About 2 cm.

*Strength.*—Strong: flexible.

*Color, distal.*—155A to 155B.

*Color, proximal.*—155A; area adjacent to stem, 155D often faintly tinged with 138A.

*Wing length.*—About 6 cm.

*Wing diameter, base.*—About 1 cm.

*Wing color, inner surface.*—155A.

*Wing color, outer surface.*—155A; area adjacent to stem, 155A often faintly tinged with 138A.

Inflorescence description: The inflorescence consists of a spathe and spadix. Inflorescences occur sporadically in clusters of 4–5 near the shoot apex.

*Spathe.*—Length: 7 cm to 8 cm. Width: 2 cm to 3 cm. Color, immature; outer surface: 149D, inner surface 149D. Color, mature; outer surface: 149D, inner surface 149D.

*Spadix.*—Length: About 3 cm to 4 cm; Female section: About 4 mm to 6 mm; Male section: About 3.0 to 3.5 cm. Width: About 4 mm to 5 mm. Color: Lower female section; stigmatic surface 15D to 15C; outer ovary surface 149D. Each spadix contains about 5 to 7 individual female flowers. Color: Upper male section; 158A.

*Peduncle.*—Length: About 5 cm to 6 cm. Diameter: About 2 mm to 3 mm. Color: 139D.

The new *Aglaonema* is apparently sterile, since no pollen has been produced on any of several inflorescences observed and no seed has been produced following controlled pollinations.

Disease/pest resistance: Plants of the new *Aglaonema* have not been observed to be resistant to pathogens or pests common to *Aglaonema.*

Temperature tolerance: Plants of the new *Aglaonema* have been observed to be tolerant to temperatures ranging from about 13° C. to about 40° C. for several hours.

It is claimed:

1. A new and distinct *Aglaonema* plant named 'UF-742-3' as illustrated and described.

* * * * *